United States Patent [19]

Maurer

[11] 4,393,232

[45] Jul. 12, 1983

[54] PREPARATION OF 3-BROMO-4-FLUORO-BENZOIC ACID

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 298,827

[22] Filed: Sep. 2, 1981

[30] Foreign Application Priority Data

Sep. 19, 1980 [DE] Fed. Rep. of Germany ....... 3035355

[51] Int. Cl.³ ............................................. C07C 51/29
[52] U.S. Cl. .................................................. 562/419
[58] Field of Search ................. 562/419; 568/316, 323

[56] References Cited

U.S. PATENT DOCUMENTS

| 1,930,449 | 10/1933 | Bruson | 562/419 |
| 2,394,268 | 2/1946 | Spencer | |
| 3,013,079 | 12/1961 | Pearson | 568/316 |
| 3,360,566 | 12/1967 | Linder | 568/323 |

FOREIGN PATENT DOCUMENTS

| 3006685 | 2/1980 | Fed. Rep. of Germany . |
| 1088788 | 10/1967 | United Kingdom . |
| 598594 | 3/1978 | U.S.S.R. ............................ 562/419 |

OTHER PUBLICATIONS

Buu-Hoi, Rec. Trav. Chim., 68, pp. 781–788 (1949).
Fuson, Chem. Rev. 15, pp. 275–309 (1934).
Olah, "Friedel Crafts and Related Reactions,", vol. III, pp. 1–18, 44–45, 159, 1517–1534 and 1547–1551 (1965).
N. N. Quang et al., Rec. Trav. Chim., Pay Bas 83, 1142–1148 (1964).

Primary Examiner—Michael L. Shippen
Attorney, Agent, or Firm—Sprung, Horn, Kramer & Woods

[57] ABSTRACT

A process for the preparation of 3-bromo-4-fluorobenzoic acid of the formula

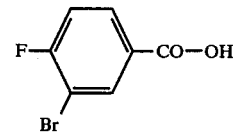

comprising reacting fluorobenzene of the formula

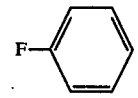

acetyl chloride in the presence of an acylation catalyst at a temperature from about 0° to 100° C., reacting the reaction mixture thereby obtained with bromine at a temperature from about 50° to 150° C., separating the resulting bromination product and reacting it with hypochlorite solution at a temperature between about 0° and 100° C. Aluminum chloride is the preferred catalyst.

5 Claims, No Drawings

PREPARATION OF 3-BROMO-4-FLUORO-BENZOIC ACID

The invention relates to an unobvious process for the preparation of 3-bromo-4-fluoro-benzoic acid.

It has already been disclosed that 3-bromo-4-fluoro-benzoic acid is obtained when 3-bromo-4-aminotoluene is diazotized in the presence of tetrafluoboric acid, the 3-bromo-toluene-4-diazonium tetrafluoborate thereby formed is pyrolyzed and the 3-bromo-4-fluorotoluene thus obtained is oxidized with potassium permanganate (see Can. J. Chem. 38 (1960), 2441–2449). However, this synthesis route described in the literature is not particularly suitable for industrial purposes since it comprises a number of complicated synthesis steps which use expensive reactants, and only low yields can be achieved.

The present invention now provides a process for the preparation of 3-bromo-4-fluoro-benzoic acid of the formula

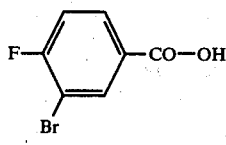

(I)

which is characterized in that fluorobenzene of the formula

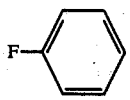

(II)

is reacted with acetyl chloride in the presence of an acylation catalyst at a temperature from about 0° to 100° C., the reaction mixture thereby obtained is reacted with bromine at a temperature from about 50° to 150° C., and the resulting bromination product is reacted, after first being isolated, with hypochlorite solution at a temperature from about 0° to 100° C.

Surprisingly, 3-bromo-4-fluoro-benzoic acid can be obtained in a simple manner and in a high yield by the process according to the present invention using inexpensive reactants.

The reaction steps of the process according to the present invention are outlined by the following equation:

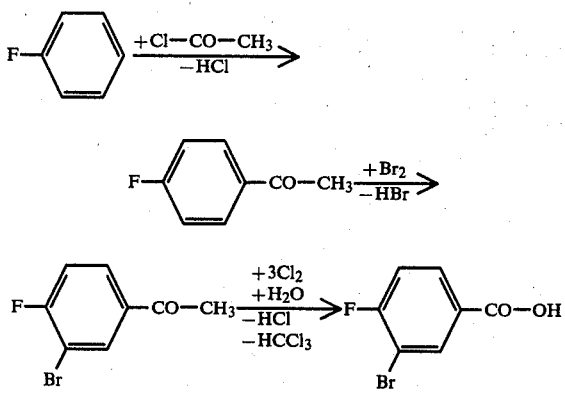

The first stage of the process according to the invention is carried out using the customary acylation catalysts known from the literature (see Methodicum Chimicum Volume 5 (1975), pages 342 and 343, Georg-Thieme-Verlag Stuttgart/Academic Press New York-San Francisco-London).

Aluminum chloride is preferably used as the catalyst.

About 0.5 to 2 moles, preferably about 1 to 1.6 moles, of acylation catalyst and about 0.9 to 1.5 moles, preferably about 1 to 1.2 moles of acetyl chloride, and in the further course of the reaction between about 0.9 and 2 moles, preferably between about 1.1 and 1.8 moles, of bromine are employed per mole of fluorobenzene. The hypochlorite solution is employed in the last stage in an amount containing between 2 and 6 moles, preferably between about 3 and 5 moles, of active chlorine.

The reaction temperature is kept between 0° and 100° C., preferably between 20° and 80° C., in the acylation stage, between 50° and 150° C., preferably between 80° and 120° C., in the bromination stage and between 0° and 100° C., preferably between 20° and 80° C., in the final haloform reaction.

All the stages of the process according to the invention are carried out under normal pressure or under a slightly increased or reduced pressure, that is to say in general between 0.1 and 10 bars, preferably between 0.5 and 5 bars.

In a preferred embodiment of the process according to the invention, the fluorobenzene and the acylation catalyst are initially introduced into the reaction vessel and the acetyl chloride is slowly added thereto. When the reaction of these components has ended, bromine is metered in (at a slightly elevated temperature within the range indicated above for the bromination stage) and, after being subsequently stirred for a short time, the mixture is poured onto ice. The bromination product, which is thereby obtained in crystalline form, is separated off by filtration and introduced into technical grade hypochlorite solution while still moist. This reaction mixture is stirred at slightly elevated temperature until the reaction has ended.

Working up can be carried out, for example, as follows: the aqueous solution is separated off from the chloroform formed, sodium bisulphite solution is added to the solution and the pH value is adjusted to 2 by adding hydrochloric acid. The product thereby obtained as crystals is isolated by filtration, dried and characterized by its melting point.

The 3-bromo-4-fluoro-benzoic acid obtainable by the process according to the invention can be used for the preparation of 3-phenoxy-4-fluoro-benzyl alcohol (see U.S. Application Ser. No. 100,538, filed Dec. 5, 1979), which is known as an intermediate product for insecticides.

For this preparation, 3-phenoxy-4-fluoro-benzoic acid is first prepared from 3-bromo-4-fluoro-benzoic acid (or the sodium or potassium salt thereof) by reaction with potassium phenolate in the presence of a copper catalyst, such as copper-II oxide, and using phenol as the diluent, at a temperature between 150° and 200° C. 3-Phenoxy-4-fluoro-benzyl alcohol is obtained from the product by reaction with a powerful reducing agent, such as lithium alanate, at a temperature between 0° and 100° C., if appropriate using a diluent, such as tetrahydrofuran (see DE-OS (German Published Specification) No. 2,915,738).

EXAMPLE

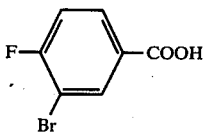

82.5 g (1.05 moles) of acetyl chloride were added dropwise to a mixture of 96 g (1 mole) of fluorobenzene and 200 g (1.5 moles) of aluminum chloride at 30°–35° C., while cooling slightly. The mixture was allowed to react at 50°–60° C. for 1 hour and 184 g (1.5 moles) of bromine were then added at 90° to 100° C. Thereafter, the mixture was subsequently stirred at 90° to 100° C. for 1 hour and the still hot mixture was then poured onto ice. The product which had precipitated was filtered off, rinsed with water and then added to 1.7 liters of technical grade hypochlorite solution while still moist. Thereafter, the mixture was first stirred at room temperature for 1 hour and was then warmed slowly to about 65° C. After 1 hour, the mixture was cooled to room temperature, the chloroform formed was separated off and 40 ml of technical grade sodium bisulphite solution were added to the clear solution. The pH was adjusted to 2 by adding concentrated hydrochloric acid and the product which had precipitated was then filtered off and rinsed with water. 190 g (87% of theory) of 3-bromo-4-fluorobenzoic acid were thus obtained in the form of a colorless powder with a melting point of 132° C.

It will be appreciated that the instant specification and examples are set forth by way of illustration and not limitation, and that various modifications and changes may be made without departing from the spirit and scope of the present invention.

I claim:

1. A process for the preparation of 3-bromo-4-fluorobenzoic acid of the formula

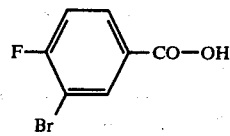

comprising reacting fluorobenzene of the formula

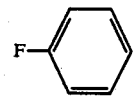

with acetyl chloride in the presence of an acylation catalyst at a temperature from about 0° to 100° C., without isolation reacting the reaction mixture thereby obtained with bromine at a temperature from about 50° to 150° C., separating the resulting bromination product and without purification reacting it with hypochlorite solution at a temperature between about 0° and 100° C.

2. A process according to claim 1, wherein the acylation catalyst is aluminum chloride.

3. A process according to claim 1, wherein about 0.5 to 2 moles of acylation catalyst, about 1 to 1.2 moles of acetyl chloride and subsequently about 0.9 to 2 moles of bromine are employed per mole of fluorobenzene.

4. A process according to claim 1, wherein the reaction with acetyl chloride is carried out at a temperature between about 20° and 80° C., the reaction with bromine is carried out at a temperature between about 80° and 120° C. and the reaction with the hypochlorite solution is carried out at a temperature between about 20° and 80° C.

5. A process according to claim 4, wherein about 0.5 to 2 moles of aluminum chloride as acylation catalyst, about 1 to 1.2 moles of acetyl chloride and subsequently about 0.9 to 2 moles of bromine are employed per mole of fluorobenzene.

* * * * *